(12) United States Patent
Feth et al.

(10) Patent No.: US 9,145,385 B2
(45) Date of Patent: Sep. 29, 2015

(54) CRYSTALLINE SALTS OF R)-3-[6-AMINO-PYRIDIN-3-YL]-2-(1-CYCLOHEXY1-1H-IMIDAZOL-4-YL)-PROPIONIC ACID (71) Applicant: Sanofi, Paris (FR)

(72) Inventors: Martin Feth, Frankfurt am Main (DE); Bruno Baumgartner, Frankfurt am Main (DE); Michael Spitzenberg, Frankfurt am Main (DE); Claudius Boehm, Frankfurt am Main (DE); Norbert Nagel, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/359,743

(22) PCT Filed: Nov. 22, 2012

(86) PCT No.: PCT/EP2012/073297
§ 371 (c)(1),
(2) Date: May 21, 2014

(87) PCT Pub. No.: WO2013/076178
PCT Pub. Date: May 30, 2013

(65) Prior Publication Data
US 2014/0329864 A1 Nov. 6, 2014

(30) Foreign Application Priority Data
Nov. 25, 2011 (EP) .................................... 11306561

(51) Int. Cl.
C07D 401/06 (2006.01)
(52) U.S. Cl.
CPC .................... C07D 401/06 (2013.01)
(58) Field of Classification Search
None
See application file for complete search history.

(56) References Cited

FOREIGN PATENT DOCUMENTS

| WO | 03013526 A1 | 2/2003 |
|---|---|---|
| WO | 2005105781 A1 | 11/2005 |
| WO | 2010130718 A1 | 11/2010 |

OTHER PUBLICATIONS

Byrn, S., Pfeiffer, R., Ganey, M., Hoiberg, C., Poochikian, G., "Pharmaceutical Solids: A Strategic Approach to Regulatory Considerations"; Pharmaceutical Research, vol. 12, No. 7, 945-954 (Jul. 1995).
Bastin, R. J., Bowker, M. J., Slater, B. J., "Salt Selection and Optimisation Procedures for Pharmaceutical New Chemical Entities" Organic Process Research Development, 2000, 4(5), 427-435 (Jul. 19, 2000).
European Search Report for European Patent Application No. EP 11 30 6561 dated Mar. 13, 2012.
Bouma, B. N., Meijers, J. C. M., J., "Thrombin-activatable fibrinolysis inhibitor (TAFI, plasma procarboxypeptidase B, procarboxypeptidase R, procarboxypeptidase U)" Thrombosis and Haemostasis, 1, 2003, 1566-1574 (Jun. 20, 2003).
Bajzar, L., "Thrombin Activatable Fibrinolysis Inhibitor and an Antifibrinolytic Pathway" Arterioscler. Thromb. Vasc. Biol. 2000, 20, 2511-2518 (Dec. 2000).

Primary Examiner — Zinna Northington Davis
(74) Attorney, Agent, or Firm — McDonnell Boehnen Hulbert & Berghoff (57) ABSTRACT The invention relates to a sodium salt of (R)-3-[6-amino-pyridin-3-yl]-2-(1-cyclohexyl-1H-imidazol-4-yl)-propionic acid which is in a crystalline form or in at least partially crystalline form as a monohydrate or anhydrate, as well as a process for the preparation of the same, methods of using such salt to treat subjects suffering from conditions which can be ameliorated by the administration of an inhibitor of the enzyme TAFIa (activated thrombin-activatable fibrinolysis inhibitor).

20 Claims, 2 Drawing Sheets

Fig. 1: X-ray powder diffraction pattern of sodium monohydrate salt of (R)-3-[6-amino-pyridin-3-yl]-2-(1-cyclohexyl-1H-imidazol-4-yl)-propionic acid Fig. 2: X-ray powder diffraction pattern of sodium anhydrate salt of (R)-3-[6-amino-pyridin-3-yl]-2-(1-cyclohexyl-1H-imidazol-4-yl)-propionic acid at 110°C

CRYSTALLINE SALTS OF R)-3-[6-AMINO-PYRIDIN-3-YL]-2-(1-CYCLOHEXY1-1H-IMIDAZOL-4-YL)-PROPIONIC ACID

This application is a national stage application under 35 U.S.C. §371 of International Application No. PCT/EP2012/073297, filed Nov. 22, 2012, the disclosure of which is explicitly incorporated by reference herein.

FIELD OF THE INVENTION

The present invention relates to crystalline sodium salts of (R)-3-[6-amino-pyridin-3-yl]-2-(1-cyclohexyl-1H-imidazol-4-yl)-propionic acid, which are in a crystalline form or in at least partially crystalline form as a monohydrate or anhydrate, as well as a process for the preparation of the same, methods of using such salts to treat subjects suffering from conditions which can be ameliorated by the administration of an inhibitor of the enzyme TAFIa (activated thrombin-activatable fibrinolysis inhibitor), and shows the structure illustrated in Formula I:

Formula I

BACKGROUND OF THE INVENTION (R)-3-[6-amino-pyridin-3-yl]-2-(1-cyclohexyl-1H-imidazol-4-yl)-propionic acid as a free acid shows the structure illustrated in Formula II:

Formula II (R)-3-[6-amino-pyridin-3-yl]-2-(1-cyclohexyl-1H-imidazol-4-yl)-propionic acid use in the preparation of a medicament for treating a patient suffering from, or subject to, conditions which can be ameliorated by the administration of an inhibitor of the enzyme TAFIa (activated thrombin-activatable fibrinolysis inhibitor), has been disclosed in WO 2005/105781.

The enzyme TAFIa is produced for example through thrombin activation from the thrombin-activatable fibrinolysis inhibitor zymogen (TAFI). The enzyme TAFI is also referred to as plasma procarboxypeptidase B, procarboxypeptidase U or procarboxypeptidase R and is a proenzyme similar to carboxypeptidase B (L. Bajzar, Arterioscler. Thromb. Vasc. Biol. 2000, pages 2511-2518).

During formation of a clot, thrombin is generated as the final product of the coagulation cascade and induces conversion of soluble plasma fibrinogen to an insoluble fibrin matrix. At the same time, thrombin activates the endogenous fibrinolysis inhibitor TAFI. Activated TAFI (TAFIa) is thus produced during thrombus formation and lysis from the zymogen TAFI through the action of thrombin; thrombomodulin in a complex with thrombin increases this effect about 1250-fold. TAFIa cleaves basic amino acids at the carboxy end of fibrin fragments. The loss of carboxy-terminal lysines as binding sites for plasminogen then leads to inhibition of fibrinolysis. Efficient inhibitors of TAFIa prevent the loss of these high-affinity lysine binding sites for plasminogen and, in this way, assist endogenous fibrinolysis by plasmin: TAFIa inhibitors have profibrinolytic effects.

In order to maintain hemostasis in the blood, mechanisms which lead to the clotting of blood and to the breaking up of clots have developed; these are in equilibrium. If a disturbed equilibrium favors coagulation, fibrin is produced in larger quantities, so that pathological processes of thrombus formation may lead to serious pathological states in humans.

Just like excessive coagulation may lead to serious pathological states caused by thrombosis, an antithrombotic treatment entails the risk of unwanted bleeding through disturbance of the formation of a necessary hemostatic plug. Inhibition of TAFIa increases endogenous fibrinolysis—without influencing coagulation and platelet aggregation—i.e. the disturbed equilibrium is shifted in favor of fibrinolysis. It is thus possible both to counter the buildup of a clinically relevant thrombus, and to increase the lysis of a pre-existing clot. On the other hand, buildup of a hemostatic plug is not impaired, so that a hemorrhagic diathesis is probably not to be expected (Bouma et al., J. Thrombosis and Haemostasis, 1, 2003, pages 1566-1574).

Inhibitors of TAFIa have already been described in the International Applications WO03/013526 and WO2005/105781. Processes for preparation are disclosed in WO2010/130718.

3-[6-amino-pyridin-3-yl]-2-(1-cyclohexyl-1H-imidazol-4-yl)-propionic acid bishydrochloride salt and its pharmacological activities have been disclosed in WO2005/105781. The bishydrochloride salt of 3-[6-amino-pyridin-3-yl]-2-(1-cyclohexyl-1H-imidazol-4-yl)-propionic acid and the free acid of 3-[6-amino-pyridin-3-yl]-2-(1-cyclohexyl-1H-imidazol-4-yl)-propionic acid have the disadvantage to occur as amorphous solids. Thus, said hydrochloride acid salts as well as said free acid cannot be purified by crystallization. Additionally, it was found that the free acid of 3-[6-amino-pyridin-3-yl]-2-(1-cyclohexyl-1H-imidazol-4-yl)-propionic acid is hygroscopic. Further it was found that (R)-3-[6-amino-pyridin-3-yl]-2-(1-cyclohexyl-1H-imidazol-4-yl)-propionic acid is chemically not stable under elevated temperature and humidity. A degradation of the molecule could be observed and the enantiomeric purity of (R)-3-[6-amino-pyridin-3-yl]-2-(1-cyclohexyl-1H-imidazol-4-yl)-propionic acid is reduced within a short time. Therefore, (R)-3-[6-amino-py- ridin-3-yl]-2-(1-cyclohexyl-1H-imidazol-4-yl)-propionic acid is not suitable for the development in a pharmaceutical formulation.

Hygroscopicity is the ability of a substance to attract and hold water molecules from the surrounding environment through either absorption or adsorption with the adsorbing or absorbing material becoming physically 'changed,' somewhat, increase in volume, stickiness, or other physical characteristic changes of the material as water molecules become 'suspended' between the material's molecules in the process. Therefore hygroscopic compounds are generally very unfavorable for use in solid pharmaceutical compositions.

It is an object of the present invention to find crystalline salts of (R)-3-[6-amino-pyridin-3-yl]-2-(1-cyclohexyl-1H-imidazol-4-yl)-propionic acid with reduced absorption or adsorption of water molecules from the surrounding environment and are chemically stable. It has been found that crystalline sodium salts of (R)-3-[6-amino-pyridin-3-yl]-2-(1-cyclohexyl-1H-imidazol-4-yl)-propionic acid have favorable reduced absorption or adsorption of water molecules from the surrounding environment and are chemically stable.

SUMMARY OF THE PRESENT INVENTION

In one embodiment the present invention relates to a sodium salt of (R)-3-[6-amino-pyridin-3-yl]-2-(1-cyclohexyl-1H-imidazol-4-yl)-propionic acid, which is in a crystalline form or in at least partially crystalline form and shows the structure illustrated in formula I:

Formula I

DETAILED DESCRIPTION OF THE INVENTION

In one embodiment the present invention relates to a sodium anhydrate salt of (R)-3-[6-amino-pyridin-3-yl]-2-(1-cyclohexyl-1H-imidazol-4-yl)-propionic acid, which is in a crystalline form or in at least partially crystalline form.

In another embodiment the invention relates to a sodium monohydrate salt of (R)-3-[6-amino-pyridin-3-yl]-2-(1-cyclohexyl-1H-imidazol-4-yl)-propionic acid, which is in a crystalline form or in at least partially crystalline form.

Polymorphism is the ability of a single compound to exist in more than one form or crystal structure. Different polymorphs represent distinct solids sharing the same molecular formula, yet each polymorph may have distinct physical properties. A single compound may give rise to a variety of polymorphic forms wherein each form may have different and distinct physical properties, such as different solubility profiles, different thermodynamic stability, different crystallization behavior, different filterability, different melting point temperatures and/or different X-ray diffraction peaks. The difference in the physical properties of different polymorphic forms results from different orientation and intermolecular interactions of adjacent molecules in the solid. Polymorphic forms of a compound can be distinguished by X-ray diffraction and by other methods such as, infrared spectroscopy or Raman spectroscopy.

"Amorphous" means a solid that exhibits in an X-ray powder diffraction pattern measured in transmission with CuKα$_1$ radiation at room temperature no characteristic reflections at degrees 2 theta which can be separated from each other by their diffraction angle or specific degree 2 theta.

In another embodiment the invention relates to a sodium salt of Formula III as a hydrate Formula III wherein n has the value from 0.7 to 1.4 and wherein n is the molar relation between water and (R)-3-[6-amino-pyridin-3-yl]-2-(1-cyclohexyl-1H-imidazol-4-yl)-propionic acid.

In another embodiment the invention relates to a sodium salt of (R)-3-[6-amino-pyridin-3-yl]-2-(1-cyclohexyl-1H-imidazol-4-yl)-propionic acid, wherein n has the value from 0.8 to 1.2 or from 0.9 to 1.1.

In another embodiment the invention relates to a crystalline sodium monohydrate salt of (R)-3-[6-amino-pyridin-3-yl]-2-(1-cyclohexyl-1H-imidazol-4-yl)-propionic acid wherein the crystalline salt exhibits in an X-ray powder diffraction pattern measured in transmission with CuKα$_1$ radiation at room temperature a characteristic reflection at degrees 2 theta of 22.2, 16.5 and 6.3, each time±0.2 degrees 2 theta.

In another embodiment the invention relates to a crystalline sodium monohydrate salt of (R)-3-[6-amino-pyridin-3-yl]-2-(1-cyclohexyl-1H-imidazol-4-yl)-propionic acid wherein the crystalline salt exhibits in an X-ray powder diffraction pattern measured in transmission with CuKα$_1$ radiation at room temperature a characteristic reflection at degrees 2 theta of 22.2, 21.8, 18.1, 16.5, 8.2 and 6.3, each time±0.2 degrees 2 theta.

In another embodiment the invention relates to a crystalline sodium monohydrate salt of (R)-3-[6-amino-pyridin-3-yl]-2-(1-cyclohexyl-1H-imidazol-4-yl)-propionic acid wherein the crystalline salt exhibits in an X-ray powder diffraction pattern measured in transmission with CuKα$_1$ radiation at room temperature a characteristic reflection at degrees 2 theta of 24.0, 22.2, 21.8, 18.8, 18.1, 16.8, 16.5, 16.0, 8.2 and 6.3, each time±0.2 degrees 2 theta.

The selection of characteristic reflections was determined by the number of reflections at a specified degree 2 theta.

Figure 1:
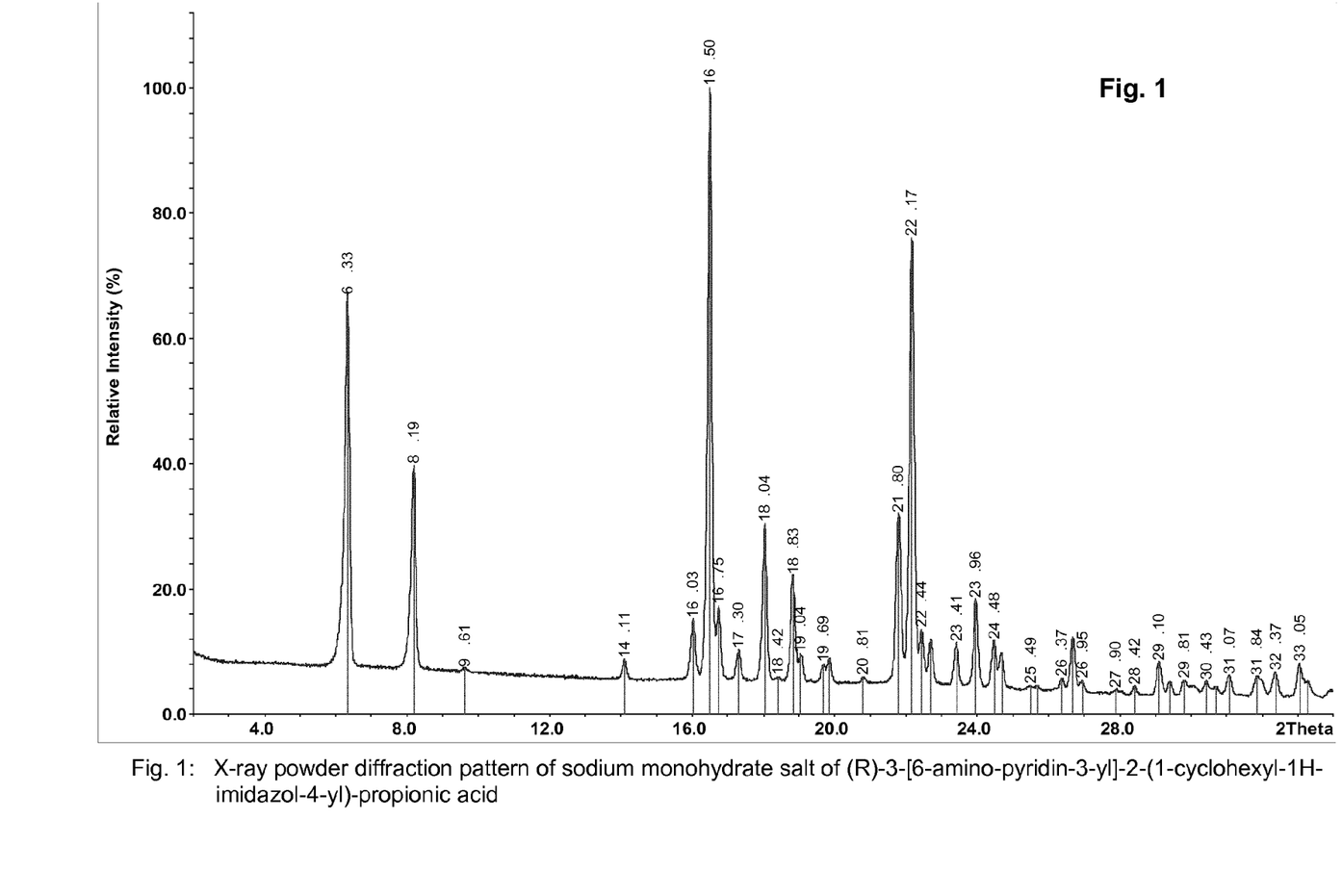
FIG. 1—X-ray powder diffraction pattern of crystalline sodium monohydrate salt of (R)-3-[6-amino-pyridin-3-yl]-2-(1-cyclohexyl-1H-imidazol-4-yl)-propionic acid, measured in transmission mode with $CuK\alpha_1$ radiation at room temperature (x-axis: diffraction angle 2theta (2θ) [°]; y-axis: relative intensity FIG. 2—X-ray powder diffraction pattern of crystalline sodium anhydrate salt of (R)-3-[6-amino-pyridin-3-yl]-2-(1-cyclohexyl-1H-imidazol-4-yl)-propionic acid, measured in transmission mode with $CuK\alpha_1$ radiation at 110° C. (x-axis: diffraction angle 2theta (2θ) [°]; y-axis: relative intensity The sodium salt of (R)-3-[6-amino-pyridin-3-yl]-2-(1-cyclohexyl-1H-imidazol-4-yl)-propionic acid may be prepared by dissolving of (R)-3-[6-amino-pyridin-3-yl]-2-(1-cyclohexyl-1H-imidazol-4-yl)-propionic acid in acetone or aqueous-acetone mixture or other suitable solvents to which the aqueous sodium base such as sodium hydroxide, disodium carbonate, sodium hydrogen carbonate or sodium ethanolate or a mixture thereof is added. Under stirring, the mixture can be heated to about 55° C. yielding a clear solution and subsequently cooling to about 1° C. yields a precipitate. The precipitate obtained can be filtered, washed with water and dried under reduced pressure.

In another embodiment the crystalline sodium monohydrate salt of (R)-3-[6-amino-pyridin-3-yl]-2-(1-cyclohexyl-1H-imidazol-4-yl)-propionic acid may also be characterized by its X-ray powder diffraction pattern substantially by the one shown in FIG. 1, which has been obtained using CuKα$_1$ radiation in transmission mode, wherein the intensities of the reflections depicted in the Figure as well as those of the reflections specified above are not a prerequisite, but may vary.

In another embodiment the crystalline sodium monohydrate salt of (R)-3-[6-amino-pyridin-3-yl]-2-(1-cyclohexyl-1H-imidazol-4-yl)-propionic acid may also be characterized by its Raman spectrum. The Raman spectrum was recorded on RXN1-Dispersive Raman spectrometer equipped with PhAT-probe head (for solids) and 785 nm diode laser (400 mW) from Kaiser Optical Systems, Ltd., USA; Software Details; Aquisition: Holograms, Kaiser; Polynomial spline background correction performed in Software: OPUS 6.5 (from Bruker Optics, Ettlingen, Germany). The characteristic wave number of the Raman shift has the following values ($cm^{-1}$) and the relative intensities are shown in brackets:

818 (31), 864 (100), 1054 (24), 1284 (26), 1561 (37), and 1613 (27), each time±4 $cm^{-1}$ In another embodiment the crystalline sodium monohydrate salt of (R)-3-[6-amino-pyridin-3-yl]-2-(1-cyclohexyl-1H-imidazol-4-yl)-propionic acid may also be characterized by its Raman spectrum. The characteristic wave number of the Raman shift has the following values ($cm^{-1}$) and the relative intensities are shown in brackets:

657 (10), 818 (31), 864 (100), 981 (15), 1030 (18), 1054 (24), 1137 (10), 1216 (21), 1266 (20), 1284 (26), 1309 (16), 1351 (10), 1363 (19), 1407 (16), 1445 (20), 1561 (37) and 1613 (27), each time±4 $cm^{-1}$ The selection of characteristic wave number was determined by the number of reflections at a specified wave number.

In another embodiment the crystalline sodium monohydrate salt of (R)-3-[6-amino-pyridin-3-yl]-2-(1-cyclohexyl-1H-imidazol-4-yl)-propionic acid may also be characterized by its Raman spectrum pattern, wherein the Raman shift is characterized by the following values ($cm^{-1}$) and the relative intensities are shown in brackets:

431 (3), 484 (3), 539 (2), 566 (6), 657 (10), 759 (8), 798 (2), 818 (31), 864 (100), 882 (8), 920 (6), 968 (9), 981 (15), 999 (3), 1030 (18), 1054 (24), 1077 (6), 1137 (10), 1186 (8), 1202 (6), 1216 (21), 1242 (4), 1266 (20), 1284 (26), 1309 (16), 1351 (10), 1363 (19), 1407 (16), 1445 (20), 1495 (3), 1561 (37), 1613 (27), each time±4 $cm^{-1}$ The intensities of the Raman shift wave numbers depicted above as well as those of the wave numbers specified above are not a prerequisite, but may vary.

The crystalline sodium monohydrate salt of (R)-3-[6-amino-pyridin-3-yl]-2-(1-cyclohexyl-1H-imidazol-4-yl)-propionic acid may also be characterized by its crystal lattice parameters which have been determined by indexing its powder pattern. The crystalline sodium monohydrate salt crystallizes in the monoclinic crystal system with a=14.109(3) Å, b=5.8202(13) Å, c=10.912(3) Å, α=90.00°, β=97.958(11°), γ=90.00°, volume=887.5(5) $Å^3$.

Moreover, crystalline sodium monohydrate salt of (R)-3-[6-amino-pyridin-3-yl]-2-(1-cyclohexyl-1H-imidazol-4-yl)-propionic acid may also be characterized by its dynamic vapor sorption (DVS) water vapor sorption and desorption isotherms measured at 25° C. As shown in the examples the sorption and desorption isotherms between 30% relative humidity and 0.4% relative humidity are almost the same (low water uptake or water desorption) wherein a water uptake of 4.0% at 70% relative humidity (RH), 11.9% at 80% RH, 38.2% at 90% RH and 67.4% at 95% RH takes place.

A useful molar relation between a sodium base such as sodium hydroxide and (R)-3-[6-amino-pyridin-3-yl]-2-(1-cyclohexyl-1H-imidazol-4-yl)-propionic acid is from 1 to 2. A further useful molar relation between sodium hydroxide and (R)-3-[6-amino-pyridin-3-yl]-2-(1-cyclohexyl-1H-imidazol-4-yl)-propionic acid is from 1.2 to 1.5.

In general, the crystalline sodium monohydrate salt of (R)-3-[6-amino-pyridin-3-yl]-2-(1-cyclohexyl-1H-imidazol-4-yl)-propionic acid may also be prepared by dissolving of (R)-3-[6-amino-pyridin-3-yl]-2-(1-cyclohexyl-1H-imidazol-4-yl)-propionic acid in a suitable solvent such as an alcohol, e.g. methanol, ethanol, 2-propanol; and can be obtained by crystallizing or recrystallizing compound of formula I, starting from a solution of compound of formula I or from a suspension of compound of formula I or from solid compound of formula I. A solution of compound of formula I, or a suspension of compound of formula I, may have been obtained at the end of the chemical synthesis of compound of formula I, or it may have been obtained by dissolving or suspending previously synthesized crude compound of formula I. The term "crude compound of formula I" comprises any form of compound of formula I, e.g. the material directly obtained from chemical synthesis, a distinct crystalline form or amorphous material of the compound of formula I.

More specifically, the crystalline salt of Formula I of the invention can be obtained by (a) providing a solution or suspension of compound of Formula I, for example by dissolving or suspending crude compound Formula I in a suitable solvent such as an alcohol, e.g. methanol, ethanol, 2-propanol; or a mixture thereof, wherein a solution of compound of Formula I generally is a clear solution and may optionally have been filtered, (b) maintaining, heating, cooling or concentrating the solution or suspension with or without agitation such as stirring, to form crystals of a desired distinct crystalline form of formula III, and (c) isolating the distinct crystalline salt of formula III.

The processes for preparing crystalline forms and solvates of compound of formula III can be performed with conventional equipment and according to standard procedures. For example, concentrating of a solution or suspension in step (b) may be done by distilling off solvent partially or totally at atmospheric pressure or at reduced pressure. Isolating of a crystalline form or solvate in step (c) may be done by any conventional technique such as filtration or vacuum filtration or centrifugation. Isolating may also comprise drying, e.g. by applying elevated temperatures and/or reduced pressure, for example at moderately reduced pressure at about room temperature, i.e. a temperature of about 18° C. to about 55° C., for example about 20° C., or at about 55° C.

In a preferred embodiment, the solution or suspension may be seeded in step (b) to promote crystallization. Seeding is preferably done with a small amount of the crystalline salt of formula III already prepared.

In another embodiment the invention relates to a crystalline sodium anhydrate salt of (R)-3-[6-amino-pyridin-3-yl]-2-(1-cyclohexyl-1H-imidazol-4-yl)-propionic acid wherein the crystalline salt exhibits in an X-ray powder diffraction pattern measured in transmission with CuKα$_1$ radiation at 110° C. a characteristic reflection at degrees 2 theta of 21.4, 16.8 and 6.1, each time±0.2 degrees 2 theta.

In another embodiment the invention relates to a crystalline sodium anhydrate salt of (R)-3-[6-amino-pyridin-3-yl]-2-(1-cyclohexyl-1H-imidazol-4-yl)-propionic acid wherein the crystalline salt exhibits in an X-ray powder diffraction pattern measured in transmission with CuKα$_1$ radiation at 110° C. a characteristic reflection at degrees 2 theta of 22.4, 21.4, 16.8, 16.4, 8.6 and 6.1, each time±0.2 degrees 2 theta.

In another embodiment the invention relates to a crystalline sodium anhydrate salt of (R)-3-[6-amino-pyridin-3-yl]-2-(1-cyclohexyl-1H-imidazol-4-yl)-propionic acid wherein the crystalline salt exhibits in an X-ray powder diffraction pattern measured in transmission with CuKα$_1$ radiation at 110° C. a characteristic reflection at degrees 2 theta of 22.4, 21.4, 18.7, 18.4, 18.2, 18.0, 17.5, 16.8, 16.4, 14.0, 8.6 and 6.1, each time±0.2 degrees 2 theta.

The selection of characteristic reflections was determined by the number of reflections at a specified degree 2 theta.

Figure 2:
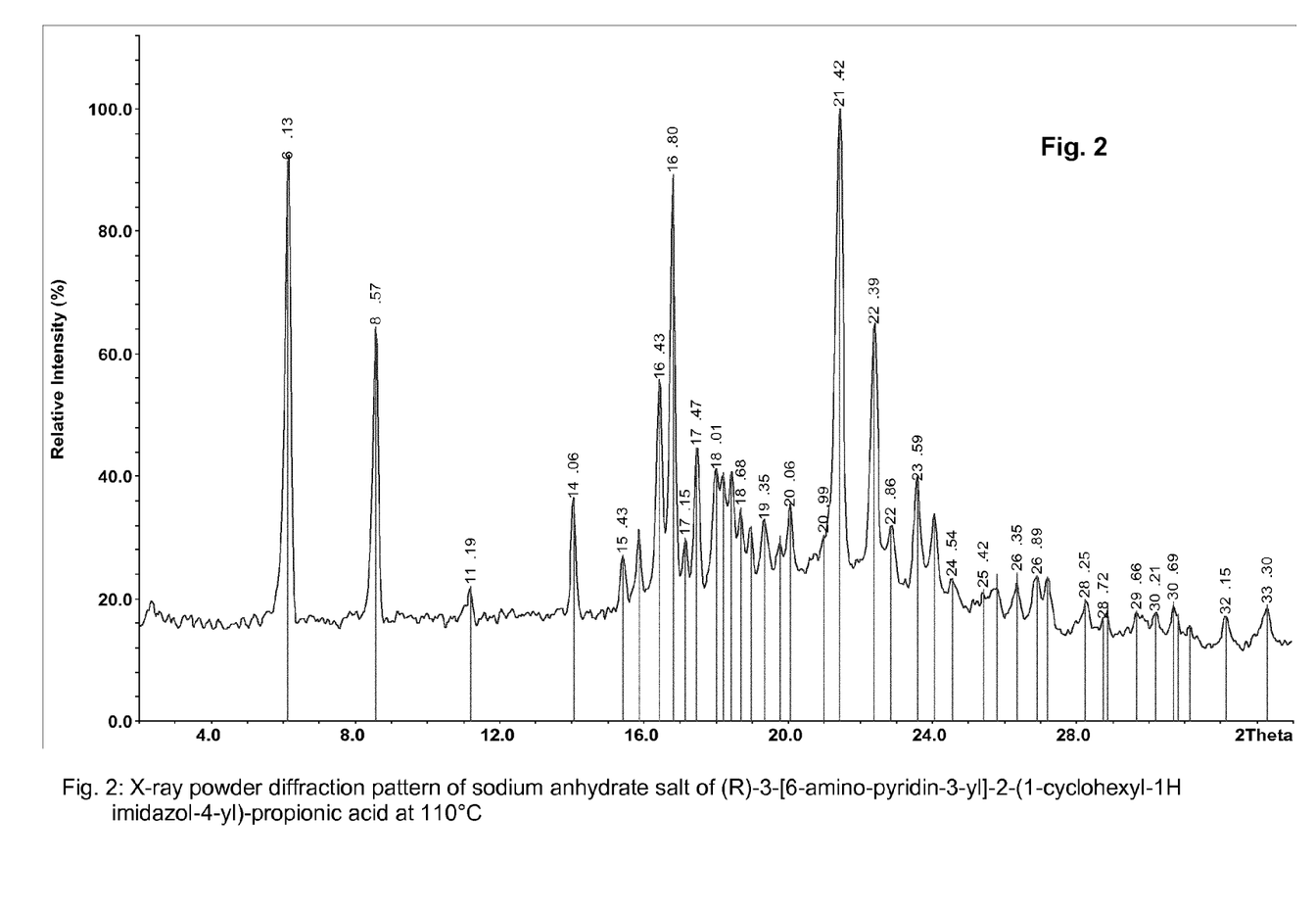

In another embodiment the crystalline sodium anhydrate salt of (R)-3-[6-amino-pyridin-3-yl]-2-(1-cyclohexyl-1H-imidazol-4-yl)-propionic acid may also be characterized by its X-ray powder diffraction pattern substantially by the one shown in FIG. 2, which has been obtained using CuKα$_1$ radiation in transmission mode, wherein the intensities of the reflections depicted in the Figure as well as those of the reflections specified above are not a prerequisite, but may vary.

In another embodiment the crystalline sodium anhydrate salt of (R)-3-[6-amino-pyridin-3-yl]-2-(1-cyclohexyl-1H-imidazol-4-yl)-propionic acid may also be characterized by its Raman spectrum. The characteristic wave number of the Raman shift has the following values (cm$^{-1}$) and the relative intensities are shown in brackets:

1604 (46), 1552 (43), 1447 (43), 1281 (46), 1262 (43), 861 (100), and 818 (49), each time±4 cm$^{-1}$ In another embodiment the crystalline sodium anhydrate salt of (R)-3-[6-amino-pyridin-3-yl]-2-(1-cyclohexyl-1H-imidazol-4-yl)-propionic acid may also be characterized by its Raman spectrum. The characteristic wave number of the Raman shift has the following values (cm$^{-1}$) and the relative intensities are shown in brackets:

1604 (46), 1552 (43), 1447 (43), 1365 (31), 1349 (34), 1281 (46), 1262 (43), 1051 (37), 861 (100), and 818 (49), each time±4 cm$^{-1}$ The selection of characteristic wave number was determined by the number of reflections at a specified wave number.

In another embodiment the crystalline sodium anhydrate salt of (R)-3-[6-amino-pyridin-3-yl]-2-(1-cyclohexyl-1H-imidazol-4-yl)-propionic acid may also be characterized by its Raman spectrum pattern, wherein the Raman shift is characterized by the following values (cm$^{-1}$) and the relative intensities are shown in brackets:

1604 (46), 1552 (43), 1502 (9), 1447 (43), 1398 (24), 1365 (31), 1349 (34), 1328 (24), 1302 (25), 1281 (46), 1262 (43), 1216 (22), 1189 (10), 1174 (9), 1156 (10), 1140 (16), 1074 (11), 1051 (37), 1029 (25), 1003, (13), 976 (17), 964 (12), 920 (6), 895 (10), 861 (100), 818 (49), 791 (6), 759 (10), 731 (6), 702 (4), 682 (5), 648 (19), 570 (3), 531 (6), 512 (4), 486 (9), 447 (9), 418 (10), 402 (7), each time±4 cm$^{-1}$ The intensities of the Raman shift wave numbers depicted above as well as those of the wave numbers specified above are not a prerequisite, but may vary.

The crystalline sodium anhydrate salt of (R)-3-[6-amino-pyridin-3-yl]-2-(1-cyclohexyl-1H-imidazol-4-yl)-propionic acid may also be characterized by its crystal lattice parameters which have been determined by indexing its powder pattern. The crystalline sodium anhydrate salt crystallizes in the triclinic crystal system at 110° C. with a=14.570(14) Å, b=5.769(5) Å, c=10.462(9) Å, α=93.87(5)°, β=97.24(4)°, γ=91.33(5)°, volume=870.0(19) Å$^3$.

In general, the crystalline sodium anhydrate salt of (R)-3-[6-amino-pyridin-3-yl]-2-(1-cyclohexyl-1H-imidazol-4-yl)-propionic acid may also be prepared by storage of already prepared crystalline sodium monohydrate salt of (R)-3-[6-amino-pyridin-3-yl]-2-(1-cyclohexyl-1H-imidazol-4-yl)-propionic acid at a relative humidity of 0.2% or heating said monohydrate crystals at temperatures from 90° C. to 120° C.

The sodium monohydrate or anhydrate salts of (R)-3-[6-amino-pyridin-3-yl]-2-(1-cyclohexyl-1H-imidazol-4-yl)-propionic acid (in the following compound of formula I) of the present invention may be useful in the prophylaxis and therapy of all disorders which can be treated by inhibition of TAFIa. Thus, the compound of formula I is suitable both for a prophylactic and for a therapeutic use in humans and is suitable both for an acute treatment and for a long-term therapy. The compound of formula I can be employed in patients suffering from impairments of wellbeing or diseases associated with thromboses, embolisms, hypercoagulability or fibrotic changes. These include myocardial infarction, angina pectoris and all other types of acute coronary syndrome, stroke, peripheral vascular disorders, deep vein thrombosis, pulmonary embolism, embolic or thrombotic events caused by cardiac arrhythmias, cardiovascular events such as restenosis following revascularization, angioplasty and similar procedures such as stent implantations and bypass operations. The compound of formula I can additionally be employed in all procedures leading to contact of the blood with foreign surfaces such as, for example, for dialysis patients and patients with indwelling catheters. The compound of formula I can be employed to reduce the risk of thrombosis after surgical procedures such as knee and hip joint operations. The compound of formula I may be suitable for the treatment of patients with disseminated intravascular coagulation, sepsis and other intravascular events associated with an inflammation and is additionally suitable for the prophylaxis and treatment of patients with atherosclerosis, diabetes and the metabolic syndrome and its sequelae. The compound of formula I may further be used to inhibit fibrotic changes of the lung such as chronic obstructive lung disease, adult respiratory distress syndrome (ARDS) and of the eye such as fibrin deposits after eye operations. The compound of formula I may also be suitable for the prevention and/or treatment of scar formation.

The invention also relates to a process for producing a pharmaceutical composition, which comprises making a suitable dosage form from a compound of the formula I with a pharmaceutically suitable and physiologically tolerated carrier and, where appropriate, further suitable active ingredients, additives or excipients.

Suitable solid or pharmaceutical formulations are, for example, granules, powder, coated tablets, tablets, (micro) capsules, suppositories, syrups, solutions, suspensions, emulsions, drops or injectable solutions, and products with protracted release of active ingredient, in the production of which normally physiologically suitable aids such as carriers, disintegrants, binders, coating agents, swelling agents, glidants or lubricants, flavorings, sweeteners and solubilizers are used. Excipients which are frequently used and which may be mentioned are magnesium carbonate, titanium dioxide, lactose, mannitol and other sugars, talc, milk protein, gelatin, starch, cellulose and its derivatives, animal and vegetable oils such as fish liver oil, sunflower, peanut or sesame oil, polyethylene glycol and solvents such as, for example, sterile water and monohydric or polyhydric alcohols such as glycerol.

The pharmaceutical products are preferably produced and administered in dosage units, where each unit comprises as active ingredient a particular dose of the compound of the formula I. In the case of solid dosage units such as tablets, capsules, coated tablets or suspensions, this dose can be up to about 1000 mg, but preferably about 50 to 300 mg and, in the case of injection solutions in ampoule form, up to about 300 mg but preferably about 10 to 100 mg.

The daily doses indicated for the treatment of an adult patient weighing about 70 kg are, depending on the activity of the compound of formula I, from about 2 mg to 1000 mg of active ingredient, preferably about 50 mg to 500 mg. However, in some circumstances, higher or lower daily doses may also be appropriate. The compound of formula I according to the invention may be administered as frequently as necessary to obtain the desired therapeutic effect. Some patients may respond rapidly to a higher or lower dose and may find much weaker maintenance doses adequate. For other patients, it may be necessary to have long-term treatments at the rate of about 1 to about 4 doses per day, in accordance with the physiological requirements of each particular patient. Generally, the active product may be administered orally about 1 to about 4 times per day. It goes without saying that, for other patients, it may be necessary to prescribe not more than one or two doses per day.

The medicaments of the invention can be administered by oral, inhalational, rectal or transdermal administration or by subcutaneous, intraarticular, intraperitoneal or intravenous injection. Intravenous injection is preferred.

As would be apparent to a person of ordinary skill in the art, once armed with the teachings of the present disclosure, when dissolved, crystalline sodium salt of formula I loses its crystalline structure, and is therefore considered to be a solution of sodium salt of formula I. All forms of the present invention, however, may be used for the preparation of liquid formulations in which crystalline sodium salt of formula I may be, for example, dissolved or suspended. In addition, the crystalline sodium salt of formula I may be incorporated into solid formulations.

The following non-limiting examples illustrate the inventors' preferred methods for preparing and using the sodium salt of formula I of the present invention.

EXAMPLES

Example 1

Preparation of (R)-3-[6-amino-pyridin-3-yl]-2-(1-cyclohexyl-1H-imidazol-4-yl)-propionic acid free acid a) (E)-2-(1-Cyclohexyl-1H-imidazol-4-yl)-3-hydroxy-but-2-enedioic acid diethyl ester 54 g (0.23 mol) (1-Cyclohexyl-1H-imidazol-4-yl)-acetic acid ethyl ester were dissolved in 300 ml absolute Ethanol. Diethyl oxalate (77 ml, 0.57 mmol), followed by sodium ethylate (23 g, 0.34 mol) were added successively thereby the temperature rose to 35° C. The mixture was allowed to cool slowly down to 25° C. within one hour. The solution was concentrated and poured into 1 liter (l) phosphate buffer (pH=6.2, c=0.8 M). The yellow-brown solid was filtered and washed with 300 ml of water. The solid was then dried under reduced pressure at 60° C. The dry residue was digested with 300 ml of preferably tert.-butyl methyl ether (MTBE) at 40° C. for 2 hours, cooled to RT, filtered and dried on air to gave 53 g (0.16 mol, 69%) (E)-2-(1-Cyclohexyl-1H-imidazol-4-yl)-3-hydroxy-but-2-enedioic acid diethyl ester as an off white solid.

$^1$H-NMR (400 MHz, $d_6$-DMSO): δ=1.17 (t, J=7.1Hz, 3H), 1.23 (t, J=7.2 Hz, 3H), 1.20-1.29 (m, 1H), 1.30-1.44 (m, 2H), 1.61-1.77 (m, 3H), 1.78-1.88 (m, 2H), 1.98-2.07 (m, 2H), 4.03 (q, J=7.1Hz, 2H), 4.10 (q, J=7.1Hz, 2H), 4.22-4.31 (m, 1H), 7.49 (d, J=1.8 Hz, 1H), 8.57 (d, J=1.7 Hz, 1H), 13.4-14.1 (bs, 1H);

HPLC: $t_R$=1.10 min (YMC J' sphere ODS H 80 20×2.1 mm, 4 μm, A: $H_2O$+0.05% TFA, B: MeCN, 4%→95% B in 2 min, 1 ml/min, 30° C.);

Mass (ES+) ($C_{17}H_{24}N_2O_5$): calculated. 366, found 337 [M+H]$^+$,

Melting point (Mp): >150° C. decomposition. (tert-butyl methyl ether; MTBE).

b) 3-(6-tert-Butoxycarbonylamino-pyridin-3-yl)-2-(1-cyclohexyl-1H-imidazol-4-yl)-propionic acid ethyl ester The compound prepared according to process step a) (5.0 g, 14.9 mmol) was suspended in 80 ml Tetrahydrofuran (THF) and Lithium hexamethyldisilazide (LiHMDS) (16.4 ml, 16.4 mmol, 1.0 M in THF) was added at room temperature (RT). The mixture was stirred for 20 min, Tetra-(n)-butylammonium iodide (catalytic) was added, followed by (5-Bromomethyl-pyridin-2-yl)-carbamic acid tert-butyl ester (4.48 g, 15.6 mmol). After one hour water (20 ml), Ethyl acetate (AcOEt; 50 ml) were added and the pH-value was adjusted to 10.5 with saturated $K_2CO_3$. The mixture was allowed stirring for 90 min. The phases were separated and the aqueous layer was extracted with AcOEt (2×20 ml). The combined organic layers were washed with brine (20 ml), dried with $MgSO_4$ and concentrated to yield a red-orange crude product. The residue was treated with 50 ml MTBE and stirred for 30 min at 60° C. After cooling to RT the solid was filtered and washed with cold MTBE to yield the title compound (3.1 g, 7.0 mmol, 47%) as a yellowish solid.

$^1$H-NMR (500 MHz, $d_6$-DMSO): δ=1.05 (t, J=7.1Hz, 3H), 1.13-1.24 (m, 1H), 1.29-1.40 (m, 2H), 1.46 (s, 9H), 1.53-1.67 (m, 3H), 1.74-1.82 (m, 2H), 1.88-1.96 (m, 2H), 3.76-3.81 (m, 1H), 3.91-4.05 (m, 3H), 7.05 (s, 1H), 7.48 (dd, J=8.6, 1.9 Hz, 1H), 7.58 (s, 1H), 7.64 (d, J=8.6 Hz, 1H), 7.99 (d, J=1.9 Hz,

1H), 9.62 (s, 1H); HPLC: $t_R$=1.00 min (YMC J' sphere ODS H 80 20×2.1 mm, 4 μm, A: $H_2O$+0.05% TFA, B: MeCN, 4%→95% B in 2 min, 1 ml/min, 30° C.);

Mass (ES+) ($C_{24}H_{34}N_4O_4$): calculated. 442, found 443 $[M+H]^+$, Mp: 161-163° C. (MTBE).

c) 3-(6-Amino-pyridin-3-yl)-2-(1-cyclohexyl-1H-imidazol-4-yl)-propionic acid ethyl ester 39.0 g (88.1 mmol) 3-(6-tert-Butoxycarbonylamino-pyridin-3-yl)-2-(1-cyclohexyl-1H-imidazol-4-yl)-propionic acid ethyl ester as prepared in process step b) were suspended in 200 ml Ethanol (EtOH) at RT. The mixture was saturated with HCl and was then refluxed for 2 h. The mixture was concentrated and the residue was treated with saturated aqueous $K_2CO_3$ (pH 9.0). The aqueous layer was extracted with AcOEt (3×200 ml). The combined organic layers were washed with brine (100 ml), dried with $MgSO_4$ and concentrated to yield the title compound (30 g, 87.6 mmol, 99%) as brown oil.

HPLC: $t_R$=0.69 min (YMC J' sphere ODS H 80 20×2.1 mm, 4 μm, A: $H_2O$+0.05% TFA, B: MeCN, 4%→95% B in 2 min, 1 ml/min, 30° C.);

Mass (ES+) ($C_{19}H_{26}N_4O_2$): calculated. 342, found 343 $[M+H]^+$.

d) (R)-3-(6-Amino-pyridin-3-yl)-2-(1-cyclohexyl-1H-imidazol-4-yl)-propionic acid ethyl ester The two enantiomers of 3-(6-Amino-pyridin-3-yl)-2-(1-cyclohexyl-1H-imidazol-4-yl)-propionic acid ethyl ester were separated by chiral chromatography:

Batches containing 540 g of 3-(6-Amino-pyridin-3-yl)-2-(1-cyclohexyl-1H-imidazol-4-yl)-propionic acid ethyl ester were filled into a column containing 20 kg of Chiralpack AD 20 μm (Ciral Technologies Europe, France) as a chiral stationary phase. Ethanol was pumped through the column until no more (S)-3-(6-Amino-pyridin-3-yl)-2-(1-cyclohexyl-1H-imidazol-4-yl)-propionic acid ethyl ester was eluted. Then a mixture containing ethanol with 0.4% of trifluoroacetic acid were pumped through the column and fractions containing (R)-3-(6-Amino-pyridin-3-yl)-2-(1-cyclohexyl-1H-imidazol-4-yl)-propionic acid ethyl ester were collected. The received title compound showed a purity of 91.7% and an ee of 99.2%. The purity was determined by the chromatography described in Example 8.

e) ((R)-3-[6-amino-pyridin-3-yl]-2-(1-cyclohexyl-1H-imidazol-4-yl)-propionic acid ethyl ester, naphtalene 1,5-disulfonic acid salt 1.50 g (5.20 mmol, 1.2 equivalents) Naphthalene-1,5-disulfonic acid were dissolved in 15 mL water. The received solution was cooled to 10° C. 1.48 g (4.32 mmol, 1.0 equivalents) (R)-3-(6-Amino-pyridin-3-yl)-2-(1-cyclohexyl-1H-imidazol-4-yl)-propionic acid ethyl ester as prepared in process step d) were dissolved in 15 mL of a acetone/water mixture 2:3 and slowly added to the naphthalene-1,5-disulfonic acid solution. The solvents were slowly evaporated by an argon gas stream until first crystals occurred. The argon gas stream is stopped and the suspension was stirred for three hours at RT (20° C. to 22° C.). The residues were filtered off and dried over night by air. 1.83 g (2.90 mmol, 67%) of the crystalline (R)-3-(6-Amino-pyridin-3-yl)-2-(1-cyclohexyl-1H-imidazol-4-yl)-propionic acid ethyl ester 1,5-naphthyldisulfonic acid salt was received as a white solid.

f) 60 g (R)-3-[6-amino-pyridin-3-yl]-2-(1-cyclohexyl-1H-imidazol-4-yl)-propionic acid ethyl ester, naphtalene 1,5-disulfonic acid salt as prepared in process step e) were stirred overnight in 480 mL 6 N hydrochloric acid. The solvent of the reaction mixture was evaporated to dryness. The dry residue was dissolved in 222 mL of water and given on a Dowex 50WX8-200 ion exchange resin. The ion exchanger was washed with water until no 1,5-naphthyldisulfonate was detected in the water after the washing process. The product was then eluted from the ion exchanger with 2.5% ammonium hydroxide solution. The product fractions were collected and the solvent of these fractions was distilled off. The obtained solid was dissolved in 500 mL water and subsequently lyophilized. 26.8 g light yellowish powder were obtained (91% yield).

Example 2

Preparation of sodium monohydrate salt of (R)-3-[6-amino-pyridin-3-yl]-2-(1-cyclohexyl-1H-imidazol-4-yl)-propionic acid by Salt Screening on a Microreactor Plate 300 μl of the R)-3-[6-amino-pyridin-3-yl]-2-(1-cyclohexyl-1H-imidazol-4-yl)-propionic acid solution of the compound prepared in Example 1 (stock solution: 250 mg R)-3-[6-amino-pyridin-3-yl]-2-(1-cyclohexyl-1H-imidazol-4-yl)-propionic acid of the compound prepared in Example 1 free acid in 30 mL methanol) were dispensed into a microreactor plate well at 18° C. 90 μl aqueous NaOH solution (1 equivalent $OH^-$ ions) were given into the well at 18° C. The microreactor plate was then covered by a lid and shaken for two hours on a vortexer at a temperature of 25° C. Subsequently the solvent was evaporated in a stream of nitrogen for 5 hours at 25° C. Afterwards 200 μl of water/methanol mixture (1:4) were added at 18° C. The microreactor plate was then covered by a lid and shaken for 5 hours on a vortexer at a temperature of 25° C. Then the lid was cooled to 2° C. for 5 hours to facilitate the nucleation of crystalline salts. After removal of the lid the solvents were allowed to evaporate at 25° C. for 5 hours in a stream of nitrogen.

Example 3

Preparation of (R)-3-[6-amino-pyridin-3-yl]-2-(1-cyclohexyl-1H-imidazol-4-yl)-propionic acid sodium monohydrate salt by Evaporative Crystallization 8.0 g (R)-3-[6-amino-pyridin-3-yl]-2-(1-cyclohexyl-1H-imidazol-4-yl)-propionic acid as prepared in Example 1 were dissolved in 106 g ethanol at 25° C. The solution was heated to 53° C. during 30 min. Within this time frame 14.4g NaOH solution (7.5 w/w-%) were dosed into the solution. After reaching 55° C. the solution was cooled in 2 h to 0° C. Subsequently the solvent was evaporated, giving a solid crystalline product (Yield: 68%), which was identified by X-ray diffraction and thermal analysis as monohydrate sodium salt of SAR126119 (Form A).

Example 4

Differential Scanning Calorimetry (DSC) of (R)-3-[6-amino-pyridin-3-yl]-2-(1-cyclohexyl-1H-imidazol-4-yl)-propionic acid sodium monohydrate salt The DSC curve of (R)-3-[6-amino-pyridin-3-yl]-2-(1-cyclohexyl-1H-imidazol-4-yl)-propionic acid sodium salt monohydrate as prepared in Example 3 was measured on a Q1000 from TA instruments in closed pan with the following method:
Equilibrate at −30° C., Ramp 10 K/min to 300° C.,
Amount of the sample as prepared in Example 3: 7.2mg.
The DSC thermogram of the crystalline material of Example 3 shows two endothermic events in range from 10° C. to 130° C., which corresponds to the loss of water.

Example 5

Thermogravimetric Analysis (TGA) of (R)-3-[6-amino-pyridin-3-yl]-2-(1-cyclohexyl-1H-imidazol-4-yl)-propionic acid sodium salt monohydrate The TGA diagram of (R)-3-[6-amino-pyridin-3-yl]-2-(1-cyclohexyl-1H-imidazol-4-yl)-propionic acid sodium salt monohydrate as prepared in Example 3 was recorded on TA Instruments TGA Q500 equipment in nitrogen atmosphere with the following method:
Equilibrate at 25° C., Ramp: 10 K/min to 350°,
Amount of the sample: 10-20 mg,
Sample purge 25 ml/min.
The TGA thermogram of the crystalline sample of Example 3 showed 4.9% weight loss between 26° C. and 150° C., which corresponds to about 1 mol of water of (R)-3-[6-amino-pyridin-3-yl]-2-(1-cyclohexyl-1H-imidazol-4-yl)-propionic acid sodium salt monohydrate.

Example 6

X-Ray Powder Diffraction (XRPD) of (R)-3-[6-amino-pyridin-3-yl]-2-(1-cyclohexyl-1H-imidazol-4-yl)-propionic acid sodium salt monohydrate X-ray powder diffraction was performed with a Stoe Stadi-P transmission diffractometer using CuKα$_1$ radiation (wavelength is 1.54060 Angström) and a linear position sensitive detector. Unless stated otherwise, X-ray powder diffraction was performed at room temperature. Samples were investigated in flat preparation. The measured data were evaluated and plotted with the Software WinXPOW V2.12.
The observed X-ray powder diffraction pattern of (R)-3-[6-amino-pyridin-3-yl]-2-(1-cyclohexyl-1H-imidazol-4-yl)-propionic acid sodium salt monohydrate as prepared in Example 3 is displayed in the FIG. 1.
The 2θ (2theta) angles in ° (degree) are specified as the number of characteristic reflections. The 2theta angles in degree have the following values in FIG. 1 and the relative intensities are shown in brackets:
6.33 (67), 8.19 (40), 9.61 (7), 14.11 (9), 16.03 (15), 16.50 (100), 16.75 (17), 17.30 (10), 18.04 (30), 18.42 (6), 18.83 (22), 19.04 (9), 19.69 (8), 19.84 (9), 20.81 (6), 21.80 (32), 22.17 (76), 22.44 (14), 22.70 (12), 23.41 (11), 23.96 (18), 24.48 (12), 24.69 (10), 25.49 (5), 25.69 (5), 26.37 (6), 26.68 (12), 26.95 (5), 27.90 (4), 28.42 (4), 29.10 (8), 29.41 (5), 29.81 (5), 30.43 (5), 30.70 (4), 31.07 (6), 31.84 (6), 32.37 (7), 33.05 (8), 33.27 (5)

Example 7

Dynamic Vapor Sorption (DVS) of (R)-3-[6-amino-pyridin-3-yl]-2-(1-cyclohexyl-1H-imidazol-4-yl)-propionic acid sodium salt monohydrate Moisture sorption/desorption isotherms were recorded on a SPS11-10μ from Projekt Messtechnik (Ulm, Germany). One cycle was run at 25° C., in which the sample was first stepwise decreased to 0% RH and then the relative humidity was stepwise increased from 0 to 95% and the weight of the sample was measured. Typical total measurement times for both cycles were about 20 to 30 hours.
The measured data for the (R)-3-[6-amino-pyridin-3-yl]-2-(1-cyclohexyl-1H-imidazol-4-yl)-propionic acid sodium salt monohydrate as prepared in Examples 2 or 3 are shown in the following table 1.

TABLE 1

| DVS Isotherm at 25° C. | | | |
|---|---|---|---|
| | Target RH (%) | Change In Mass (%) Sorption | Change In Mass (%) Desorption |
| Cycle 1 | 30.1 | | 0.1 |
| | 20.0 | | −0.1 |
| | 10.0 | | −0.6 |
| | 0.2 | | −4.4 |
| | 10.0 | −3.7 | |
| | 20.0 | −0.2 | |
| | 30.0 | 0.2 | |
| | 40.0 | 0.6 | |
| | 50.0 | 0.9 | |
| | 60.0 | 1.5 | |
| | 70.0 | 4.0 | |
| | 75.0 | 8.2 | |
| | 80.1 | 11.9 | |
| | 85.1 | 17.7 | |
| | 90.0 | 38.2 | |
| | 94.9 | 67.4 | |

"RH" means relative humidity; the relative humidity of an air-water mixture is defined as the ratio of the partial pressure of water vapor in the mixture to the saturated vapor pressure of water at a prescribed temperature.
DVS showed desorption of −4.4% water at 0.2% RH accompanied by a phase transition from the monohydrate phase into the anhydrate phase (detected by Raman spectroscopy and XRPD). Upon rehydration at 20% RH the original monohydrate phase was regained. The monohydrate phase of (R)-3-[6-amino-pyridin-3-yl]-2-(1-cyclohexyl-1H-imidazol-4-yl)-propionic acid sodium salt monohydrate showed high water uptake of 4.0% at 70% RH, 11.9% at 80% RH, 38.2% at 90% RH and 67.4% at 95% RH for the (R)-3-[6-amino-pyridin-3-yl]-2-(1-cyclohexyl-1H-imidazol-4-yl)-propionic acid sodium salt monohydrate.

Example 8

Preparation of (R)-3-[6-amino-pyridin-3-yl]-2-(1-cyclohexyl-1H-imidazol-4-yl)-propionic acid sodium anhydrate salt by drying (R)-3-[6-amino-pyridin-3-yl]-2-(1-cyclohexyl-1H-imidazol-4-yl)-propionic acid sodium monohydrate salt at Low Humidity The anhydrate sodium salt of (R)-3-[6-amino-pyridin-3-yl]-2-(1-cyclohexyl-1H-imidazol-4-yl)-propionic acid sodium was prepared by storage of the (R)-3-[6-amino-pyridin-3-yl]-2-(1-cyclohexyl-1H-imidazol-4-yl)-propionic acid sodium monohydrate salt in a SPS11-10p device from Projekt Messtechnik (Ulm, Germany) at 25° C. and 0.2% relative humidity. The crystalline phase of the anhydrate was identified by Raman spectroscopy.

Example 9

Preparation of (R)-3-[6-amino-pyridin-3-yl]-2-(1-cyclohexyl-1H-imidazol-4-yl)-propionic acid sodium anhydrate salt by heating (R)-3-[6-amino-pyridin-3-yl]-2-(1-cyclohexyl-1H-imidazol-4-yl)-propionic acid sodium monohydrate salt above 90° C.

The anhydrate sodium salt of (R)-3-[6-amino-pyridin-3-yl]-2-(1-cyclohexyl-1H-imidazol-4-yl)-propionic acid was prepared by heating of the (R)-3-[6-amino-pyridin-3-yl]-2-(1-cyclohexyl-1H-imidazol-4-yl)-propionic acid sodium monohydrate salt on a hot stage device from Linkam Scientific Instruments (UK) to a temperature of 120° C. The crystalline phase of the anhydrate was identified by Raman spectroscopy and XRPD.

Example 10

X-Ray Powder Diffraction (XRPD) of (R)-3-[6-amino-pyridin-3-yl]-2-(1-cyclohexyl-1H-imidazol-4-yl)-propionic acid sodium salt anhydrate X-ray powder diffraction was performed with a Stoe Stadi-P transmission diffractometer using CuKα$_1$ radiation (wavelength is 1.54060 Angström) and a linear position sensitive detector. Unless stated otherwise, X-ray powder diffraction was performed at 110° C. Samples were investigated in flat preparation. The measured data were evaluated and plotted with the Software WinXPOW V2.12.

The observed X-ray powder diffraction pattern of (R)-3-[6-amino-pyridin-3-yl]-2-(1-cyclohexyl-1H-imidazol-4-yl)-propionic acid sodium salt anhydrate as prepared in Examples 8 and 9 is displayed in the FIG. 2.

The 2v (2theta) angles in ° (degree) are specified as the number of characteristic reflections. The 2theta angles in degree have the following values in FIG. 2 and the relative intensities are shown in brackets:

6.13 (91), 8.57 (64), 11.19 (22), 14.06 (36), 15.43 (27), 15.87 (31), 16.43 (55), 16.80 (89), 17.15 (30), 17.47 (45), 18.01 (41), 18.19 (41), 18.43 (41), 18.69 (35), 18.96 (32), 19.35 (32), 19.78 (30), 20.06 (35), 20.99 (30), 21.42 (100), 22.39 (64), 22.86 (32), 23.59 (39), 24.04 (33), 24.54 (23), 25.42 (22), 25.79 (24), 26.35 (24), 26.89 (24), 27.19 (24), 28.25 (20), 28.72 (16), 28.84 (19), 29.66 (18), 30.21 (18), 30.69 (19), 30.80 (17), 31.15 (16), 32.15 (17), 33.30 (19), 34.27 (16), 34.46 (15), 35.09 (16)

Example 11

Differential Scanning Calorimetry (DSC) of (R)-3-[6-amino-pyridin-3-yl]-2-(1-cyclohexyl-1H-imidazol-4-yl)-propionic acid sodium anhydrate salt The DSC curve was measured on a Mettler Toledo DSC 821$^e$ type instrument in punched pan with the following method:

Equilibrate at 25° C., Ramp: 10 K/min to 350° C.,

Amount of the sample prepared in Example 3: 2-3 mg.

The DSC thermogram of a crystalline sample of the compound as prepared in Example 3 showed two endothermic events in range of 80° C. to 130° C. corresponding to the loss of water. The formed sodium anhydrate salt form above 130° C. shows a melting endotherm with onset of 266.1° C.

Example 12 DVS, Comparison Experiment (R)-3-[6-amino-pyridin-3-yl]-2-(1-cyclohexyl-1H-imidazol-4-yl)-propionic acid as prepared in Example 1 was used for the measurement.

The measurement was performed as disclosed in Example 7 with (R)-3-[6-amino-pyridin-3-yl]-2-(1-cyclohexyl-1H-imidazol-4-yl)-propionic acid (free acid, amorphous) and the received data are shown in the following table 2.

TABLE 2

| | Target RH (%) | Change In Mass (%) Sorption | Change In Mass (%) Desorption |
|---|---|---|---|
| Cycle 1 | 30.1 | | 1.7 |
| | 20.0 | | 1.1 |
| | 10.1 | | 0.3 |
| | 0.4 | | −1.6 |
| | 10.0 | −0.5 | |
| | 20.0 | 0.5 | |
| | 30.0 | 1.9 | |
| | 40.1 | 3.9 | |
| | 50.0 | 6.6 | |
| | 60.1 | 9.6 | |
| | 70.0 | 13.4 | |
| | 75.0 | 15.0 | |
| | 80.1 | 16.9 | |
| | 85.1 | 20.1 | |
| | 89.9 | 25.1 | |
| | 95.0 | 32.3 | |

DVS Isotherm at 25° C.

DVS shows a strong water uptake of 3.9% at 40% RH, 6.6% at 50% RH, 9.6% at 60% RH, 13.4% at 70% RH, 16.9% at 80% RH, 25.1% at 90% RH and 32.3% at 95% RH for (R)-3-[6-amino-pyridin-3-yl]-2-(1-cyclohexyl-1H-imidazol-4-yl)-propionic acid (free acid, amorphous).

The invention claimed is:

1. Sodium salt of (R)-3-[6-amino-pyridin-3-yl]-2-(1-cyclohexyl-1H-imidazol-4-yl)-propionic acid as a monohydrate in a crystalline form or in at least partially crystalline form, wherein the crystalline salt exhibits in an X-ray powder diffraction pattern measured in transmission with CuKα$_1$ radiation at room temperature a characteristic reflection at degrees 2 theta of 22.2, 16.5 and 6.3, each ±0.2 degrees 2 theta.

2. The sodium salt according to claim 1, wherein the crystalline salt exhibits in an X-ray powder diffraction pattern measured in transmission with CuKα$_1$ radiation at room temperature a characteristic reflection at degrees 2 theta of 22.2, 21.8, 18.1, 16.5, 8.2 and 6.3 each ±0.2 degrees 2 theta.

3. The sodium salt according to claim 1, wherein the crystalline salt exhibits in an X-ray powder diffraction pattern measured in transmission with CuKα$_1$ radiation at room temperature a characteristic reflection at degrees 2 theta of 24.0, 22.2, 21.8, 18.8, 18.1, 16.8, 16.5, 16.0, 8.2 and 6.3 each ±0.2 degrees 2 theta.

4. The sodium salt according to claim 1, which is characterized by an x-ray powder diffraction pattern substantially in accordance with that shown in FIG. 1.

5. Sodium salt of (R)-3-[6-amino-pyridin-3-yl]-2-(1-cyclohexyl-1H-imidazol-4-yl)-propionic acid as an anhydrate in a crystalline form or in at least partially crystalline form, wherein the crystalline salt exhibits in an X-ray powder diffraction pattern measured in transmission with CuKα$_1$ radiation at room temperature a characteristic reflection at degrees 2 theta of 21.4, 16.8 and 6.1, each ±0.2 degrees 2 theta.

6. The sodium salt according to claim 5, wherein the crystalline salt exhibits in an X-ray powder diffraction pattern measured in transmission with CuKα$_1$ radiation at room temperature a characteristic reflection at degrees 2 theta of 22.4, 21.4, 16.8, 16.4, 8.6 and 6.1 each ±0.2 degrees 2 theta.

7. The sodium salt according to claim 5, wherein the crystalline salt exhibits in an X-ray powder diffraction pattern measured in transmission with CuKα$_1$ radiation at room temperature a characteristic reflection at degrees 2 theta of 22.4, 21.4, 18.7, 18.4, 18.2, 18.0, 17.5, 16.8, 16.4, 14.0, 8.6 and 6.1 each ±0.2 degrees 2 theta.

8. The sodium salt according to claim 5, which is characterized by an x-ray powder diffraction pattern substantially in accordance with that shown in FIG. 2.

9. The sodium salt of claim 1, wherein the monohydrate is in a crystalline form.

10. The sodium salt of claim 2, wherein the monohydrate is in a crystalline form.

11. The sodium salt of claim 4, wherein the monohydrate is in a crystalline form.

12. The sodium salt of claim 5, wherein the anhydrate is in a crystalline form.

13. The sodium salt of claim 6, wherein the anhydrate is in a crystalline form.

14. The sodium salt of claim 8, wherein the anhydrate is in a crystalline form.

15. A pharmaceutical composition comprising the sodium salt of (R)-3-[6-amino-pyridin-3-yl]-2-(1-cyclohexyl-1H-imidazol-4-yl)-propionic acid according to claim 1 and a pharmaceutically acceptable carrier or excipient.

16. A pharmaceutical composition comprising the sodium salt of (R)-3-[6-amino-pyridin-3-yl]-2-(1-cyclohexyl-1H-imidazol-4-yl)-propionic acid according to claim 5 and a pharmaceutically acceptable carrier or excipient.

17. A process for the preparation of the sodium salt as a monohydrate according to claim 1, comprising
dissolving (R)-3-[6-amino-pyridin-3-yl]-2-(1-cyclohexyl-1H-imidazol-4-yl)-propionic acid in a suitable solvent wherein a solution or suspension is formed;
heating, cooling or concentrating the solution or suspension to form crystals of crystalline form of formula III, Formula III and
isolating the distinct crystalline salt of formula III.

18. A process for the preparation of a sodium salt of (R)-3-[6-amino-pyridin-3-yl]-2-(1-cyclohexyl-1H-imidazol-4-yl)-propionic acid as an anhydrate in a crystalline form or in at least partially crystalline form, wherein the crystalline salt exhibits in an X-ray powder diffraction pattern measured in transmission with CuKα$_1$ radiation at room temperature a characteristic reflection at degrees 2 theta of 21.4, 16.8 and 6.1, each ±0.2 degrees 2 theta, the process comprising:
storing the sodium monohydrate salt of (R)-3-[6-amino-pyridin-3-yl]-2-(1-cyclohexyl-1H-imidazol-4-yl)-propionic acid prepared according to claim 12 at a relative humidity of 0.2%,
or heating sodium monohydrate salt of (R)-3-[6-amino-pyridin-3-yl]-2-(1-cyclohexyl-1H-imidazol-4-yl)-propionic acid prepared according to claim 12 at temperatures from 90° C. to 120° C.

19. The process of claim 17, wherein the suitable solvent is an alcohol.

20. The process of claim 19, wherein the alcohol is methanol, ethanol, 2-propanol, or a mixture thereof.

* * * * *